United States Patent [19]

Stewart

[11] 4,224,072

[45] Sep. 23, 1980

[54] PIT AND FISSURE SEALANT FOR TEETH

[75] Inventor: Lygia Stewart, Salt Lake City, Utah

[73] Assignee: University of Utah, Salt Lake City, Utah

[21] Appl. No.: 941,063

[22] Filed: Sep. 11, 1978

[51] Int. Cl.$^3$ ................................. C09K 3/00
[52] U.S. Cl. ........................ 106/35; 106/85
[58] Field of Search .................. 106/35, 85

[56] References Cited

U.S. PATENT DOCUMENTS

| | | | |
|---|---|---|---|
| 3,787,900 | 1/1974 | McGee | 106/35 |
| 4,149,893 | 4/1979 | Aoki et al. | 106/35 |

OTHER PUBLICATIONS

Chem. Abst. 52:860f, 1958.

*Primary Examiner*—Theodore Morris
*Attorney, Agent, or Firm*—Trask & Britt

[57] ABSTRACT

An inorganic, enamel-like sintered coating (or sealant) adherent to teeth is disclosed. Materials very similar to tooth enamel, e.g., hydroxyapatite, combined with a low melting eutectic constitute the coating. This material can be applied to the tooth and sintered in place with a laser. The presence of the low melting eutectic lowers the energy requirement for sintering.

5 Claims, No Drawings

PIT AND FISSURE SEALANT FOR TEETH

BACKGROUND OF THE INVENTION

1. Field:

The instant invention relates to compositions for application to teeth to seal the tiny pits and fissures which habor bacteria and are significant sources of cavities, particularly in children's teeth. Pit and fissure sealants presently in use are generally organic polymers which are cured with catalysts. Polymeric coatings are effective for a short period, generally less than about one to two years, primarily because such organic coatings do not match the chemical composition of the tooth enamel, are more susceptible to abrasion and chemical attack than an inorganic coating and do not match the thermal, chemical or mechanical properties of the tooth enamel.

2. Prior Art:

Prior attempts have been made to use a laser to fuse tooth enamel to prevent caries or to fuse to the enamel a compatible material, such as hydroxyapatite. These attempts are reported by Lobene et al, "Interaction of Carbon Dioxide Laser Radiation with Enamel and Dentin", J. Dental Research, March-April 1968, pp. 311 et. seq. The fusion of hydroxyapatite to tooth enamel failed while direct application of a laser beam to the enamel caused degradation of the enamel.

OBJECTS OF THE INVENTION

It is an object of the instant invention to provide an inorganic chemical coating for teeth to provide a durable, longer-lasting pit and fissure sealant.

A further object of the instant invention is to provide an inorganic coating having chemical, thermal and mechanical properties substantially identical to the tooth enamel.

Another object of the instant invention is to provide an inorganic coating which is sintered in in situ.

A further object of the instant invention is to provide an inorganic coating which can be sintered at a temperature sufficiently low as to be sintered by a low-energy laser beam.

Other objects of the invention are to provide an inorganic coating material compatible with tooth enamel which can be sintered into a tooth without harming the tooth and to provide an inorganic coating material which can be applied uniformly to a tooth in a wet state.

SUMMARY OF THE INVENTION

A coating composition of an inorganic, sintered ceramic material adherent to a tooth and having thermal, mechanical and chemical properties approximating that of tooth enamel has been invented. Phosphate compositions useful in this invention are hydroxyapatite, which has the formula $Ca_{10}(PO_4)_6(OH)_2$ and tricalcium phosphate, $Ca_3(PO_4)_2$. Hydroxyapatite is generally preferred for the purposes of this invention, however, the presence of tricalcium phosphate in substantial quantities in hydroxyapatite-eutectic compositions has not evidence any deleterious properties. The addition of a low-melting eutectic such as a lithium fluoride, magnesium fluoride, calcium fluoride mixture lowers the sintering temperature of hydroxyapatite to a temperature which can be easily and effectively obtained by a low-energy laser beam.

These materials are sinterable at a low temperature considering the inorganic reactions which must occur and which generally occur only at a very elevated temperature. This is particularly true of the hydroxyapatite-eutectic materials.

Generally, the durable inorganic coating is applied as a liquid slurry to a tooth. After the liquid dries, it is subjected to a low-energy laser beam to sinter the coating and adhere same to the tooth substrate. The coating material is applied to a tooth and sintered by direction of low-energy laser, particularly a $CO_2$ laser, for a period sufficient to effect sintering. The coating, in sintered form, has thermal, mechanical and chemical properties substantially similar to the tooth enamel.

The application of the very reactive material, as a result of careful precipitation to obtain very fine particles, in a liquid slurry appears beneficial. Fusion of hydroxyapatite applied from a liquid slurry appeared to proceed readily in the absence of a flux material when high energy densities were utilized, i.e., energy densities in excess of 360 joules/cm² although much lower than by a factor of 10 than the energy levels used by Lobene et al, supra.

Hydroxyapatite And Tricalcium Phosphate Materials

Synthetic hydroxyapatite, $CA_{10}(PO_4)_6(OH)_2$, and tricalcium phosphate, $Ca_3(PO_4)_2$, have compositions substantially identical to natural tooth enamel. These may be fused to a tooth by inclusion of a low-melting eutectic in the mixture.

A flux or eutectic compound containing alkali metals, alkaline earth metals, Group III metals and ammonium ions are particulaly useful. Halides, phosphates and oxides of the above form fluxes especially sintered to lowering the sintering temperature of the coating composition to less than 700° C. and preferably into the range of about 300° C. to 400° C. Akali metal halides and alkaline earth metal halides, and mixtures thereof, are useful as low-melting eutectic materials. Fluorides are the most useful of the halide compounds. Other eutectic materials include NaF, $NH_4HF_2$, $NH_4H_2PO_4$, $AlF_3$, CaO and $P_2O_5$, the latter two being most effective when used in combination.

Low-melting eutectics which are generally preferred are compositions containing lithium fluoride, magnesium fluoride and calcium fluoride. Optionally, aluminum fluoride may be included. A typical eutectic composition is one containing 59% lithium fluoride, 27.9% magnesium fluoride, 13.1% calcium fluoride. An aluminum fluoride containing composition utilized in the invention contains 58.1% lithium fluoride, 27.5% magnesium fluoride, 12.9% calcium fluoride, and 1.5% aluminum fluoride. The eutectic materials are mixed mechanically and then melted at about 700° C. to 900° C. While still in a liquid state, the materials are poured onto a steel plate to cool and then ground to 200 mesh. Although other eutectic mixtures may be utilized, it is preferred to use a eutectic which, when mixed with hydroxyapatite lowers the sintering temperature to a range of about 200° C. to about 400° C. A fluoride salt or a mixture of fluoride salts possess some advantages inasmuch as the presence of fluoride in the tooth coating composition may be advantageous as a caries preventative.

Hydroxyapatite may be prepared by dissolving 0.167 moles of calcium nitrate hydrate, $Ca(NO_3)_2.4H_2O$, in enough water to make approximately a one molar solution. This is adjusted to pH 11 with concentrated ammonia and then diluted to approximately 0.5 molar solution. Approximately 0.100 moles of ammonium hypophosphate, $(NH_4)_2HPO_4$, are dissolved in enough water to make approximately a 0.6 molar solution. This is adjusted to pH 11 with concentrated ammonia and then diluted to about a 0.27 molar solution. The ammonium phosphate solution is dripped into the calcium nitrate solution with constant stirring. A white precipitate forms immediately. The resulting solution is then stirred for 24 hours at room temperature.

After stirring the mixture is treated in one of three ways: (1) a precipitate is allowed to settle and most of the supernatant is decanted and the remaining solution is concentrated to various concentrations; (2) a precipitate is filtered, washed well and then dried at about 20° C. to 90° C. after which it is ground to 200 mesh; and (3) the precipitate is centrifuged and washed well; then either resuspended in water or dried as in step (2).

A further procedure may be utilized except that equimolar amounts of calcium nitrate and ammonium hydrophosphate are used and the materials are always filtered and dried as in the second step above.

These techniques for preparing hydroxyapatite can result in the preparation of substantial quantities of tricalcium phosphate. Tricalcium phosphate is more prevalent in hydroxyapatite compositions which have not been washed thoroughly and in compositions which are sintered at higher temperatures. The presence of substantial quantities of tricalcium phosphate do not appear to be detrimental to the performance of the coating composition.

The disclosed techniques used to prepare hydroxyapatite are practiced in order to obtain a very fine precipitate of hydroxyapatite. Fine precipitates appear to sinter at a lower temperature to a more dense, more adherent, less porous coating. Beside the techniques disclosed herein, fine precipitates may be obtained by following the procedure outlined by Jarcho et al, "Hydroxyapatite Synthesis and Characterization in Dense Polycrystalline Form", Journal of Material Science 11, (1967) pp. 2027-2035.

A coating composition comprising generally about 30% eutectic and about 70% hydroxyapatite by weight is a preferred mixture. Slightly lower, e.g., down to about 10% by weight, or greater amounts, e.g., up to about 50% by weight, of eutectic may be utilized some with decrease in effectiveness.

The coating composition comprises hydroxyapatite and eutectic dispersed in either ethanol or water. Various weight percentages of powder in liquid can be used. Percentages between 25° and 50% have been used effectively. A thoroughly dispersed slurry is utilized and materials are sprayed or brushed or otherwise coated as evenly as possible onto the tooth. Thicknesses between about 10 to 200 microns are generally applied. Single or multiple coatings may be applied.

For experimental purposes in the laboratory, teeth have been mounted on a belt which rotates at about 12 to 13 cm/sec through the spray of the airbrush. The teeth may also be sprayed manually holding the airbrush with the teeth stationary. In application to a dental patient's teeth, a shield is employed which shields the gum and the face and exposes only those teeth desired to be coated. The shield would be used to protect teeth during application of the liquid sinterable material and also during sintering of the coating with a laser beam. As indicated, the shield could be used to shield one quadrant at one time. Coatings on the lingual side of teeth may be sintered by reflecting the laser beam or by guiding the beam by an appropriately designed glass fiber.

After the hydroxyapatite materials are applied the curing is effected with an infrared laser having a continuous power output of 0-3 watts at a wavelength of about 10.6 microns. Energy densities between 20 and 360 joules per square centimeter using pulse durations of 0.125 to 1.0 seconds were utilized. Multiple coatings and firings are also useful. The multiple application technique usually results in a smoother surface of the sintered material. It is very desirable to keep the power requirements as low as possible so that the sintering cycle does not injure the tooth enamel or the tooth pulp. The tooth enamel under too stringent firing conditions could be cracked and the pulp, if over heated, could be injured, causing the tooth to die. Thus, the criterion for the materials are that they be easily sintered very quickly at relatively low temperatures.

Prior to application of the liquid material, the tooth enamel is cleaned well and etched lightly with a dilute acid.

EXAMPLE 1

Hydroxyapatite was synthesized as previously described using 1.0 mole $Ca(NO_3)_2 \cdot 4H_2O$ to 1.0 mole $(NH_2)_2HPO_4$. Material was filtered, washed well, and dried overnight at 90° C. Hydroxyapatite was ground to 200 mesh and mixed mechanically with eutectic of composition 59 mol% LiF, 27.9 mol% $MgF_2$ and 13.1 mol% $CaF_2$ which had also been ground to 200 mesh. Hydroxyapatite to eutectic ratio was 70:30 by weight.

Material was dispersed in Ethanol, powder to liquid ratio was 10:11 by weight. It was then sprayed onto teeth which had been polished with 3200 mesh Buehler polish and etched for 60 sec. in 50% $H_3PO_4$. Thickness used were 30-150μ. Coated teeth were fired with a $CO_2$ laser for 0.5 and 1.0 seconds at power density 211 watts/cm².

Material was well sintered on tooth. Teeth were then placed in 5% Lactic and 5% Acetic acid for three weeks. There was no change in material after this test. Teeth were then stored in an aqueous solution for 6 months with no change in material.

EXAMPLE 2

Hydroxyapatite was synthesized as previously described using 1.67 moles $Ca(NO_3)_2 \cdot 4H_2O$ to 1.0 mole $(NH_4)_2HPO_4$. Most of supernatent was decanted off and enough eutectic of composition 58.1 mol% LiF, 27.5 mol% $MgF_2$, 12.9 mol% $CaF_2$, and 1.5 mol% $AlF_3$, which had been ground to 200 mesh, was added to result in a hydroxyapatite to eutectic ratio of 70:30 by weight. Slurry was then concentrated to about 21% powder by weight.

Above slurry was then sprayed on teeth which had been cleaned and etched for 60 sec with 50% $H_3PO_4$. A thickness of about 20μ was applied and the teeth were fired with a $CO_2$ laser for 0.125 and 0.25 second at power density of 190 watts/cm². A second coating of about 20μ was then applied and again fired under the same circumstances.

Resulting material was well sintered to the tooth and had relatively smooth surface.

Teeth were then placed in a floresent dye visible under ultraviolet light (zyglo) for 24 hours and then sectioned and viewed under UV light for evidence of dye penetration. There was none. Teeth were then subjected to thermal cycling between 15° and 45° C. for 30 seconds at each water temperature. 850 total cycles were done. There was no change after test. Teeth also exhibited no change after soaking in aqueous solution.

EXAMPLE 3

Hydroxyapatite was synthesized as previously described using 1.67 moles $Ca(NO_3)_2.4H_2O$ to 1.0 mole $(NH_4)_2HPO_4$. Material was centrifuged, washed, recentrifuged, washed, and dispersed in $H_2O$. Eutectic of composition 58.1 mol% LiF, 27.5 mol% $MgF_2$, 12.9 mol% $CaF_2$ and 1.5 mol% $AlF_3$ which had been ground to 200 mesh was added to result in a hydroxyapatite to eutectic ratio of 70:30 by weight. Resulting slurry was concentrated to about 25% powder by weight.

Above slurry was then sprayed on teeth which had been cleaned and etched for 60 seconds with 50% $H_3PO_4$. A coating was applied of about $20\mu$ and the teeth were then fired for 0.125 seconds at power density 168 watts/cm². Then a second coating of $20\mu$ was applied and fired again at same energy density.

Material was well sintered to teeth and showed no change after soaking in aqueous medium.

Half of the teeth fired were subjected to thermal cycling (as described in Example 2) for 520 cycles. Then all teeth were placed in fluorsent dye visible under UV light, and viewed under UV light for evidence of dye penetration. There was none on either thermal cycled samples or uncycled samples.

EXAMPLE 4

Hydroxyapatite was synthesized as previously described using 1.67 moles $Ca(NO_3)_2.4H_2O$ to 1.0 mole $(NH_4)_2HPO_4$. Material was centrifuged, washed well, dried at 25° C., and then ground to 200 mesh. Hydroxyapatite was then mechanically mixed with eutectic of composition 58.1 mol% LiF, 27.5 mol% $MgF_2$, 12.9 mol% $CaF_2$, and 1.5 mol% $AlF_3$ which had also been ground to 200 mesh. Hydroxyapatite to eutectic ratio was 70:30 by weight.

Material was dispersed in $H_2O$, powder to liquid ratio was 10:11 by weight. Resulting slurry was sprayed on teeth which had been cleaned and etched for 60 seconds with 50% $H_3PO_4$. A coating of $20-40\mu$ was applied and teeth were fired with a $CO_2$ laser for 0.5 and 1.0 seconds at power densities of 211 to 316 watts/cm². A second coating was applied for same thickness and teeth were fired again under same conditions.

Materials were very smooth and well sintered to tooth surface. Fired materials showed no change after soaking in aqueous medium and thermal cycling for 600 cycles.

EXAMPLE 5

Hydroxyapatite was synthesized as previously described using 1.0 mole $Ca(NO_3)_2.4H_2O$ to 1.0 mole $(NH_4)_2HPO_4$. Material was filtered, washed well, dried at 90° C., and ground to 200 mesh. Eutectic of composition 59 mol% LiF, 27.9 mol% $MgF_2$, and 13.1 mol% $CaF_2$, which had been ground to 200 mesh, was mixed mechanically with the hydroxyapatite in weight percents of 20 to 30%.

Material was applied to teeth by pushing it into the crevaces on the occlusal surface. Coated teeth were fired for 0.25 seconds at 505 and 537 watts/cm². Material was well sintered to tooth surface and showed no change after soaking in aqueous solution.

Similar results were achieved when $NH_4HF_2$, $NH_4H_2PO_4$, NaF or $AlF_3$ were added to the above eutectic compositions, especially when said compounds were added in quantities of about 1.5 to about 9.3 mole percent.

Similar results were obtained through the use of power densities up to 200 watts/cm² for the same time intervals.

I claim:

1. A sinterable coating composition capable of being sintered in situ on a tooth surface by a low power laser, said coating composition comprising a slurry of hydroxyapatite and a sufficient amount of a compatible eutectic containing a fluoride compound to lower the sintering temperature of said composition to less than about 700° C.

2. The coating composition of claim 1, wherein said eutectic is present at about 10% to about 50% by weight of said coating.

3. The coating composition of claim 1 wherein calcium triphosphate is present in addition to hydroxyapatite.

4. The coating composition of claim 1 wherein said eutectic is present in sufficient quantities to enable said composition to sinter at about 200° C. to about 400° C.

5. The coating composition of claim 1 wherein said eutectic is an admixture consisting essentially of lithium fluoride, magnesium fluoride, and calcium fluoride.

* * * * *